(12) United States Patent
Tseng et al.

(10) Patent No.: US 7,121,666 B2
(45) Date of Patent: Oct. 17, 2006

(54) APPARATUS AND METHOD FOR THE KINETIC ANALYSIS OF TEAR STABILITY

(76) Inventors: Scheffer C. G. Tseng, 10000 SW. 63 Pl., Pinecrest, FL (US) 33156; Eiki Goto, 4-10-3, Matsugaoka, Kugenuma, Fujisawa, Kanagawa (JP)

(*) Notice: Subject to any disclaimer, the term of this patent is extended or adjusted under 35 U.S.C. 154(b) by 0 days.

(21) Appl. No.: 10/131,665

(22) Filed: Apr. 24, 2002

(65) Prior Publication Data

US 2002/0180929 A1 Dec. 5, 2002

Related U.S. Application Data

(60) Provisional application No. 60/286,408, filed on Apr. 25, 2001.

(51) Int. Cl.
*A61B 3/14* (2006.01)

(52) U.S. Cl. ...................................... 351/206
(58) Field of Classification Search ............... 351/200, 351/205, 206, 211, 212, 221, 246; 356/237.1, 356/239.1, 239.7, 601; 600/558
See application file for complete search history.

(56) References Cited

U.S. PATENT DOCUMENTS

| | | | | |
|---|---|---|---|---|
| 4,747,683 A | * | 5/1988 | Doane | 351/206 |
| 5,110,200 A | * | 5/1992 | Snook | 351/212 |
| 5,867,250 A | * | 2/1999 | Baron | 351/212 |
| 6,213,605 B1 | * | 4/2001 | D'Souza et al. | 351/212 |
| 6,299,305 B1 | * | 10/2001 | Miwa | 351/200 |
| 6,447,119 B1 | * | 9/2002 | Stewart et al. | 351/212 |
| 2002/0163623 A1 | * | 11/2002 | Hirohara et al. | 351/212 |

OTHER PUBLICATIONS

Goto, E. and Tseng, SCG, "Kinetic Analysis of Tear Interference Images in Aqueous Tear Deficiency Dry Eye Before and After Punctal Occlusion," *Invest. Ophthal*, 44 (5): 1897–1905 (May 2003).

Goto, E. and Tseng, SCG, "Differentiation of Lipid Tear Deficiency Dry Eye by Kinetic Analysis of Tear Interference Images," *Arch Ophthalmol*, 121: 173–180 (Feb. 2003).

* cited by examiner

*Primary Examiner*—Brian L. Casler
*Assistant Examiner*—John R. Sanders
(74) *Attorney, Agent, or Firm*—Arendt & Associates Intellectual Property Group; Jacqueline M. Arendt (57) ABSTRACT

An apparatus and method for the kinetic analysis of tear interference is disclosed. The apparatus includes a light source for illuminating a tear film of a cornea, an optical train for modifying the light before it reaches the cornea and after it is the carrier of an image from the cornea, an image recorder to record a series of images of the illuminated tear film, and an image output for providing the series of images to a display; the series of images illustrating a tear film dispersion pattern indicative of a tear stability condition. The method includes the steps of illuminating the film on a cornea of said eye with light, recording a series of images of the illuminated film, and outputting the series of images to a display. The series of images illustrating at least one of a lipid film spread and a tear film dispersion pattern indicative of a tear stability condition.

15 Claims, 6 Drawing Sheets

APPARATUS AND METHOD FOR THE KINETIC ANALYSIS OF TEAR STABILITY

CROSS-REFERENCES TO RELATED APPLICATIONS

This application claims the benefit of U.S. Provisional Application Ser. No. 60/286,408, filed on Apr. 25, 2001, entitled KINETIC ANALYSIS OF THE TEAR INTERFERENCES PATTERN.

TECHNICAL FIELD

The present invention relates generally to the analysis and evaluation of eye conditions. In particular, the present invention relates to an apparatus and method for the kinetic analysis of tear interference pattern and lipid film spread.

BACKGROUND OF THE INVENTION

Blinking of the eyelids causes the corneas of the eyes to be covered with tear fluid, including a superficial lipid layer, in the form of a thin film. The ability to maintain a stable tear film imparts the ocular surface with qualities relating to clear vision, comfort and defense against injury and infection. Over the time between blinks, the tear film gradually thins out to a point where the tear film loses cohesion and breaks up. The time required for the tear film to break up (hereinafter referred to as BUT (break up time)) can be understood as a function of the dispersion of the lipid layer. The lipid layer functions to protect moisture from evaporating, to help the tear film to be thin and stable, to help lubricate the lid movement across the eye ball, and to prevent the condition known as dry eye.

Dry eye is the hallmark of an unstable tear film condition. Dry eye can be expressed as a result of lipid tear deficiency (LTD) in a subject possessing meibomian gland disease (MGD), or an aqueous tear deficiency (ATD) in a subject possessing lacrimal gland disease. With regard to ATD, the diagnostic criteria rely on the measurement of tear production. Diagnosis of LTD has been indirect, using either meibography to examine the changes in morphology of the meibomian gland, or digital compression to determine meibum expressibility, or meibometry to determine lid margin meibum, or rapid tear evaporation, or dye staining techniques.

Unstable tear film conditions typically are measured as a function of BUT. One of the preferred BUT measuring methods of the prior art is the incorporation of sodium fluorescein to the tear film. The sodium fluorescein gives a yellowish-green color to the tear film and causes the term film to fluoresce in the presence of a portion of the visible light spectrum (typically blue light). Observation of the tear film is made directly by using a slit lamp, having a blue filter to allow for the passage of light having wavelengths of approximately 330 to 400 nm. The elapsed time between a blink and the development of darkened regions in the fluorescent tear film is defined as the BUT.

Another method used to measure BUT uses an observed grid pattern imaged onto the tear film. The observed image quality depends upon the tear film's stability, yielding a smooth surface and concealing the irregularities of the surface of the cornea.

Yet another method of investigating the tear film is through tear interference. Typically, a single static image is obtained to partially quantify the thickness of the tear film, particularly the lipid film. One such static image providing device is the DR-1®, manufactured by Kowa (Tokyo, Japan). Previously, it has been assumed that such static images are roughly representative of, and provide data approximately relating to, lipid film thickness. However, because a static image is taken without being consistently timed from the onset of the blink, it is impossible to determine important information relevant to diagnosing and treating LTD, such as speed and direction of lipid spread or dispersion. Although there are examples in the prior art of continuous video recording of tear interference during blinking, these video images fail to analyze the kinetics of the tear film to indicate tear stability conditions. Moreover, the prior art video imaging fails to quantify color information of the tear interference images, to further indicate tear stability conditions.

Accordingly, a need exists for a method and apparatus for the kinetic analysis of tear interference, particularly for illustrating a tear film dispersion pattern, indicative of a tear stability condition. Additionally, there is a need for a method and apparatus for the kinetic analysis of lipid film spread that illustrates a lipid film dispersion pattern indicative of a tear stability condition. Moreover, there is a further need for the dispersion pattern to provide quantifiable color information.

SUMMARY OF THE INVENTION

The present invention eliminates the above-mentioned needs by providing a method and apparatus for the kinetic analysis of tear interference, particularly for illustrating a tear film dispersion pattern indicative of a tear stability condition. The present invention further permits the kinetic analysis of lipid film spread, that illustrates a lipid film dispersion pattern indicative of a tear stability condition and can display a dispersion pattern in a manner that provides quantifiable color information.

In accordance with the present invention, there is provided an apparatus for the kinetic analysis of tear interference. The apparatus includes: a light source for illuminating a tear film of a cornea, an optical train for modifying the light before it reaches the cornea and after it is the carrier of an image from the cornea, an image recorder to record a series of images of the illuminated tear film, and an image output for providing the series of images to a display; the series of images illustrating a tear film dispersion pattern indicative of a tear stability condition.

The present invention is further directed to a method of analyzing the kinetics of a tear film of an eye. The method includes the steps of: illuminating the tear film of a cornea with light, recording a series of images of the illuminated tear film, and outputting the series of images to a display; the series of images illustrating a tear film dispersion pattern indicative of a tear stability condition.

DETAILED DESCRIPTION OF THE INVENTION

Figure 1:
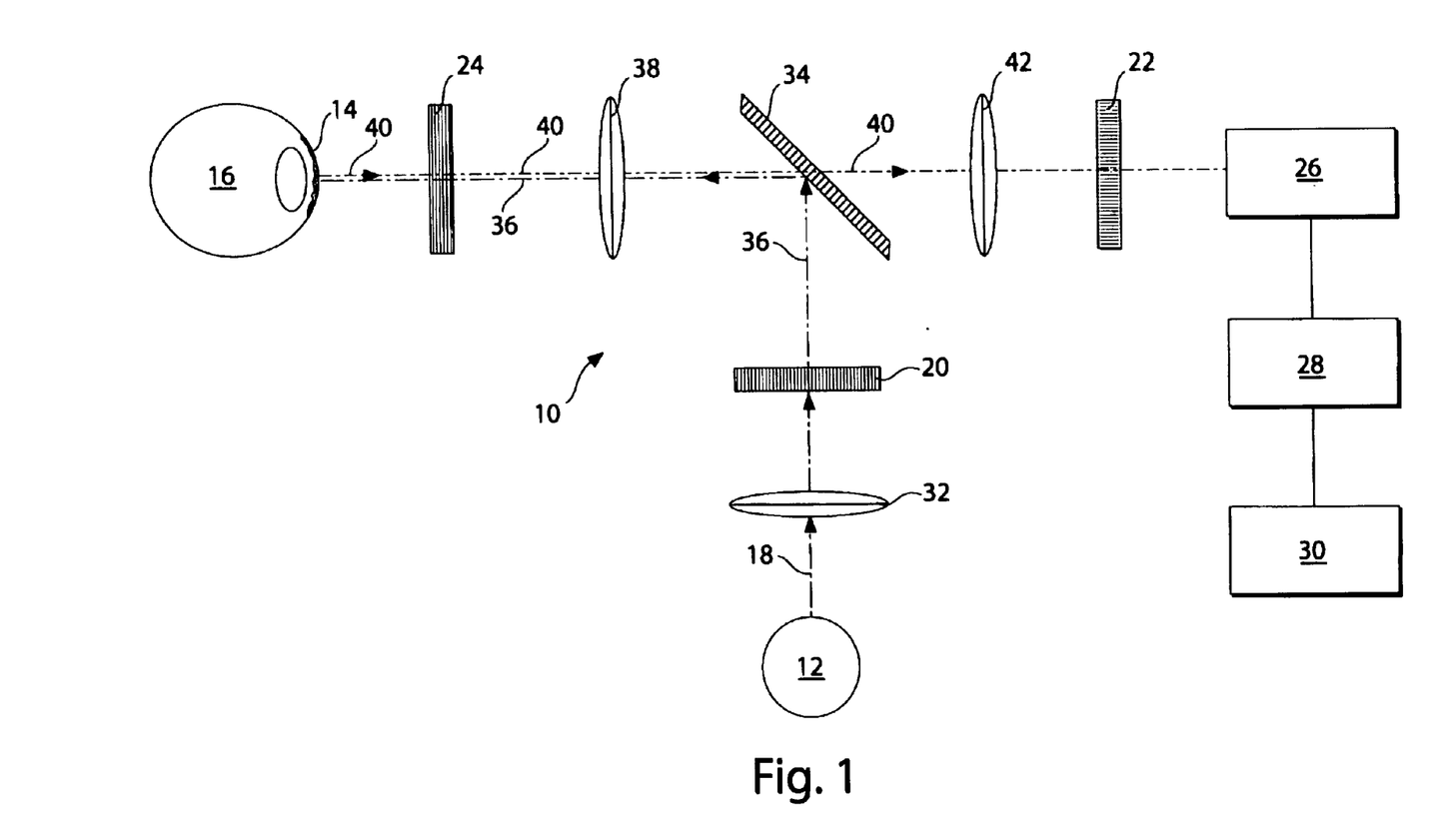
FIG. 1 is block diagrammatic illustration of the preferred embodiment of the present invention.

Referring now to FIG. 1, a preferred embodiment of the present invention is illustrated as kinetic analysis apparatus 10. Kinetic analysis apparatus 10 includes: light source 12, for illuminating a tear film 14 of an eye 16 with light 18; polarizers 20 and 22 to polarize light 18, quarter-wave plate 24; an image recorder 26, to record a series of images of the illuminated tear film 14; and image output 28, to provide the series of images to a display 30.

As shown in FIG. 1, light source 12 generates light 18, which passes through a lens 32 and the polarizer 20, where it is polarized. Light, such as light 12, can be regarded either as a flow of particles, or as an electromagnetic wave. Light, regarded as a waveform, can be considered to be oscillating up/down, oscillating left/right and all directions in-between. A polarizing filter, such as polarizer 20 or 22, only allows to pass therethrough the component of the oscillating light 18 that is directed in the polarizing direction of the filter. Once polarized, light 18 passes to half-mirror 34, where it is reflected towards eye 16.

Polarized light 36 is reflected off of half-mirror 34, passes through lens 38 and quarter-wave plate 24 to reach eye 16. A quarter-wave plate is a plate of doubly refracting crystal, that introduces a phase difference of one-quarter cycle between the ordinary and extraordinary rays passing through it perpendicularly; and can be used to measure refraction and to convert polarized light, as discussed next. A quarter-wave plate consists of a carefully adjusted thickness of a birefringent material, such that the light associated with the larger index of refraction is retarded by 90° in phase (a quarter wavelength) with respect to that associated with the smaller index. The birefringent material is cut so that the optic axis is parallel to the front and back plates of the plate 24. Any linearly polarized light that strikes the plate will be divided into two components, with different indices of refraction. One of the useful applications of this device 24 is to convert linearly polarized light to circularly polarized light and vice versa. This is accomplished by adjusting the plane of the incident light so that it makes 45° angle with the optic axis, as shown in FIG. 1. This gives equal amplitude o-(ordinary) and e-(extraordinary) waves. When the o-wave is slower, as in calcite, the o-wave will fall behind by 90° in phase, producing circularly polarized light.

Polarized light 36 illuminates tear film 14, and reflects back off of the eye 16. The reflected light 40 passes through plate 24 in order to be re-polarized. Polarized reflected light 40 passes through lens 38 and half-mirror 34, through lens 42 and polarizer 22. Lenses 32, 38, and 42 are composed of transparent material, such as glass, and have two opposite regular curved surfaces (double convex) that serve to focus light 18, 36, and 40 respectively, in order to form an image at image recorder 26. The described optical elements are part of a DR-1® camera.

Figure 2:
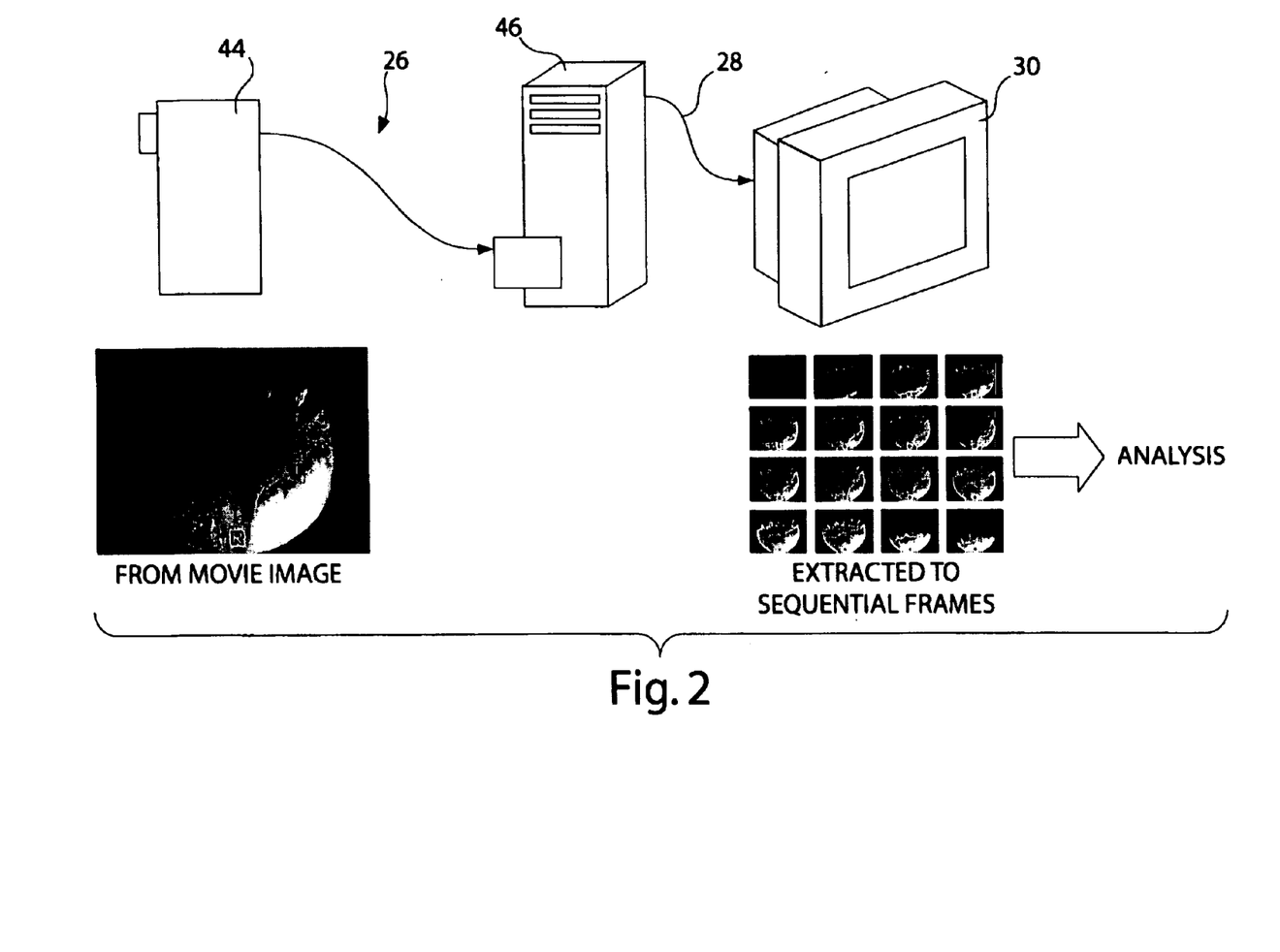
FIG. 2 is a block diagrammatic illustration of the camera recorder-output and display portion of the preferred embodiment illustrated in FIG. 1.

As illustrated in FIG. 2, image recorder 26 includes a tear interference observation camera 44, a processor 46 with frame grabbing software, and image output 28 to provide the series of images to display 30. It is preferred that tear interference observation camera 44 be a high quality charge-coupled device (CCD) camera such as the previously mentioned DR-1®, thus having the advantages of acquiring an image of a central cornea of an eye and focusing sharply on the tear lipid, without the background of the iris of the eye. A CCD is a light-sensitive integrated circuit that stores and displays the data for an image in such a way that each pixel (picture element) in the image is converted into an electrical charge the intensity of which is related to a color in the color spectrum. A CCD in a digital camera improves resolution compared with older technologies. Another asset of the CCD is its high degree of sensitivity. A CCD can produce an image in extremely dim light, and its resolution does not deteriorate when the illumination intensity is low, as is the case with conventional cameras. It is also preferred that camera 44 have a magnification of at least 10×, and most preferably a magnification of 12×, so as to allow for observations of at least 8 mm in diameter of the cornea. It is additionally preferred that display 30 be a display device including, but not limited to, computer monitors and televisions.

In order to obtain kinetic recordings of the tear film for analysis, the camera 44 is linked to processor 46 with frame grabbing software. Examples of such frame grabbing software include, but are not limited to, FlashBus MV lite® manufactured by Integral Technologies, Inc. (Indianapolis, Ind.), and the like. The sequential images are digitized as uncompressed files, such as AVI format files, using image capture software, including, but not limited to ImagePro 4.1®. An AVI (Audio Video Interleaved) file is a sound and motion picture file that conforms to the Microsoft Windows Resource Interchange File Format (RIFF) specification. AVI files (which end with an avi extension) require a special player that can be included with a variety of computer software packages. The frame rate can be set as 5.18 frames per second and recorded for 29 seconds, resulting in 150 frames. It is preferred that the sequential images representing blink and inter-blink intervals be chosen randomly, then extracted as an uncompressed file, such as a TIFF file, which can be made into a composite image and used to minimize the loss of image quality and change of color information during analysis. This image quality and color information is exported via image output 28 to display 30.

The completion of tear lipid spread is defined as the time interval from time 0 to the time of the frame that has a lipid film image that shows a stable and identical pattern. If the image does not achieve a stable pattern throughout the entire inter-blink interval, such an image is defined as "unstable", and the entire inter-blink interval is used for analysis of the speed of tear lipid spread. The time for tear lipid spread is then is calculated according to video speed, for example the video speed being adjusted to 1.93 sec/frame.

During any given inter-blink time (IBT), sequential images show an image of the tear film. If the tear film image is stable until the next blink, it is judged to have stable tear dynamics. If the tear film image does not reach stability by the next blink, it is judged to have unstable tear dynamics. In addition, the preferred embodiment of the present invention allows for the ability to view the pattern of tear lipid spread. The propagation of the spread can demonstrate the tear dynamics further. A horizontal propagating streak is indicative of tear stability, while a vertical propagating streak is indicative of tear instability.

Moreover, tear lipid layer thickness can be determined from look up tables (LUT). Measurements are conducted using image sequence analysis. The dominant color of the image is used for analysis. Care should be taken in that LUT is a simulation of color and should be different by optical system of tear interference including light source wavelength and specular angle.

Figure 5A:
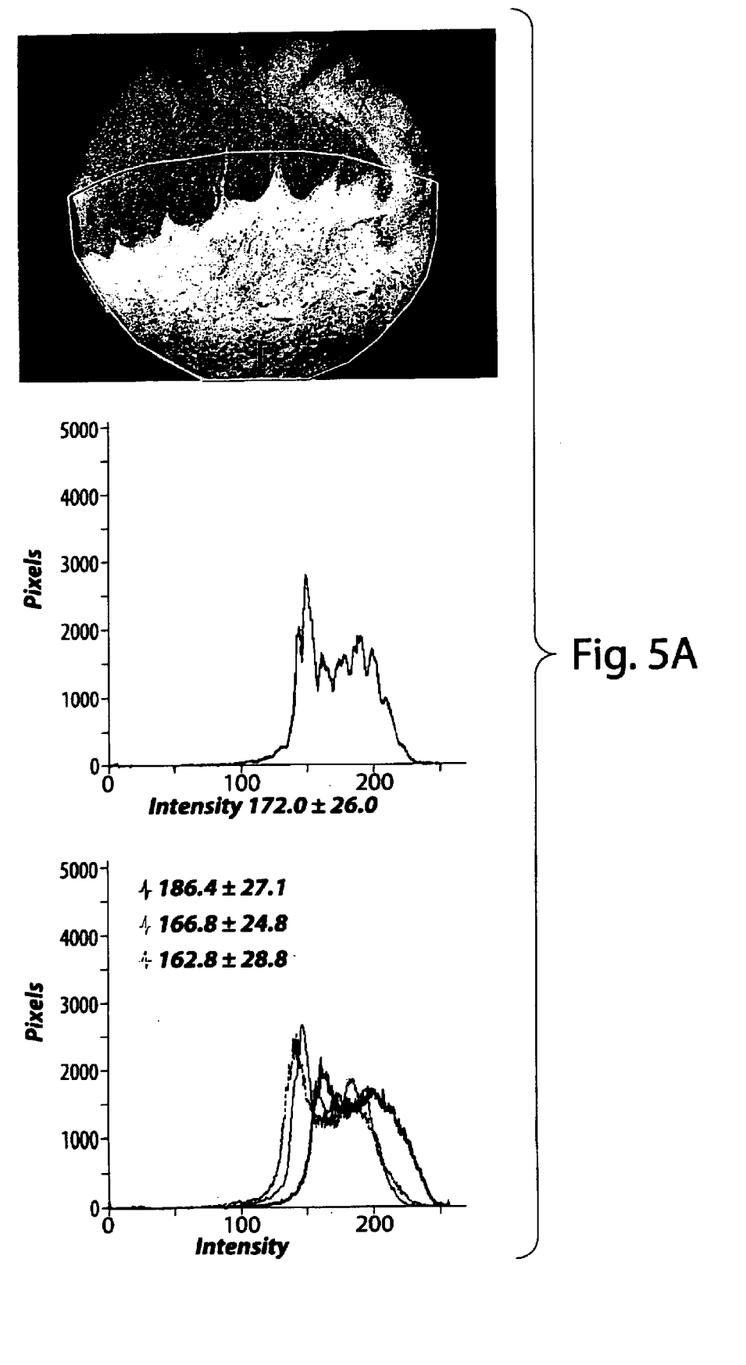
FIG. 5a is a tear interference images showing a polygonal area applied for color intensity, color analysis for a normal subject.
Figure 5B:
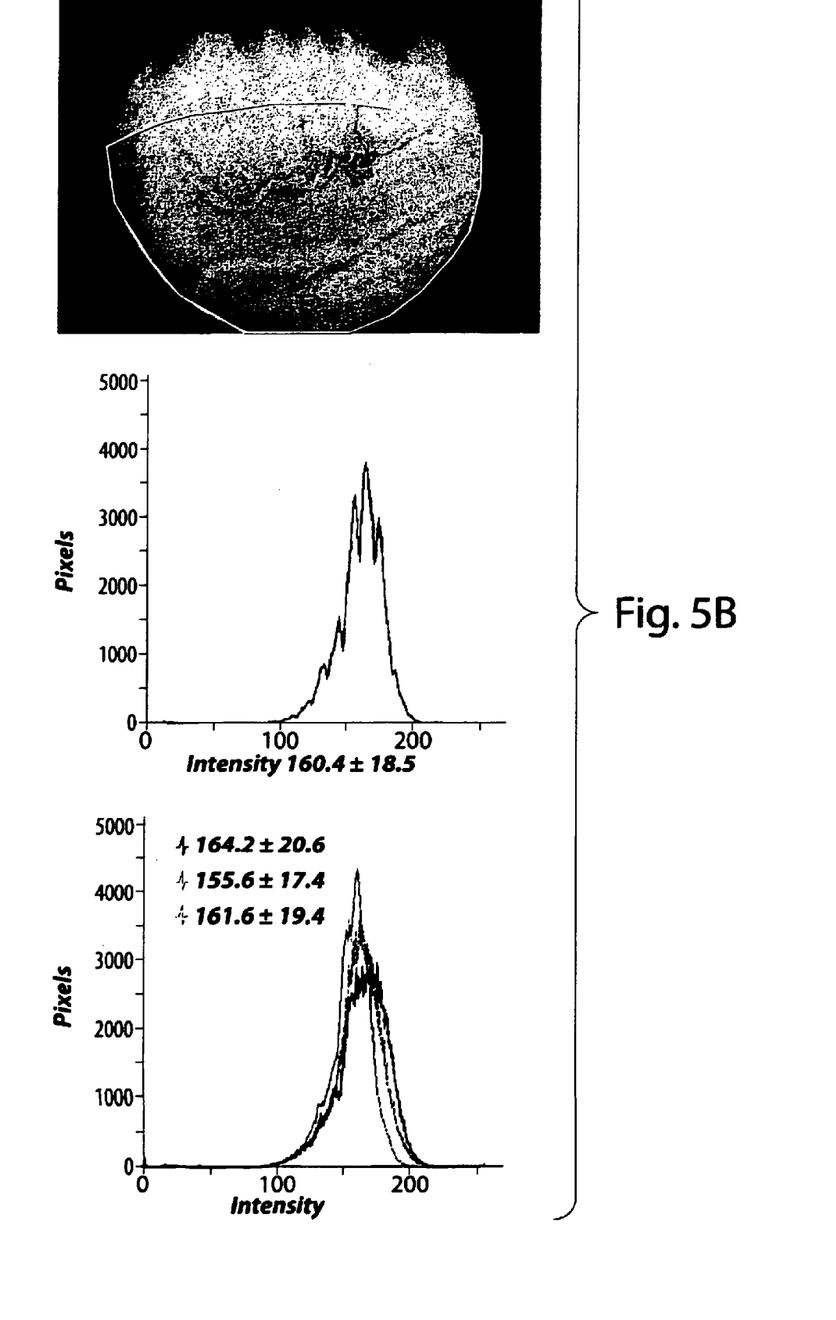
FIG. 5b is a tear interference images showing a polygonal area applied for color intensity, color analysis for an ATD subject.

In the principle of tear interference, white broadband light source thin film interference phenomenon, color intensity information indicates thin layer thickness information. In practice, to directly compare the thickness of a particular area is difficult, so color information comparisons can be performed to compare the thickness information using an intensity histogram of the particular area. The average value is the average brightness value indicating thin layer thickness of an interference image. For that reason, a system of minimal loss of color information should be chosen. Polygonal area is applied during full open IBT period, as shown in FIGS. 5a and 5b, so that this area would contain a minimal area of lid and lashes images. These images are colored black and affect the color image analysis.

Fisher's exact test was used for analysis of data of a categorical scale. Fisher's exact test is an alternative to the chi-squared test for testing the hypothesis that some proportion of interest differs between two groups. It has the advantage that it does not make any approximations, and so is suitable for small sample sizes.

For ordinal scale with value, Mann-Whitney U-test is applied. The Mann-Whitney U test is used to take a list of items and inspect it in order to see if a specified category of items tends to occur towards the beginning or end of the list. If the rank sum of a category varies more than could be expected by chance, the items can be assumed to be in nonrandom order. This is useful to test some ordinal or continuous parameter of variation with an unknown distribution. A level <0.05 is to be considered as statistically significant.

observed. A stripe-shaped streaking lipid film would then cover this dark uniform layer. As a result, the vertical streaking image is seen.

In a study employing eight LTD patients, the images of five patients never reached a stable image compared to the normal image, and were judged unstable (p=0.0048). It was demonstrated that with a long period of $3.54\pm1.86$ sec, the lipid film could reach a stable image (p=0.0003). During the entire period of blinking, the faint white colored narrow and vertical patterned lipid film appeared (dark image) on dark background color image, suggesting an insufficiently thin layer, by way of the interference principle. Estimated thickness from LUT was $53.8\pm20.0$ nm, significantly thinner than normal (p=0.0166). Color intensity histogram average was $122\pm10.8$, a significantly darker image than normal; thus indicating a thinner lipid layer (p=0.0007) than in a normal; subject. Additionally, the normal state is thicker than that found in the LTD patients who do not have a sufficient amount of lipid on the ocular surface. Furthermore, with regard to evenness, all LTD patients had a significantly uneven distribution of lipid (p=0.0000).

ATD Patients

After each frame of the sequence was analyzed in all ATD patients, it was observed that the lipid film spread upward from the lower lid margin following blinking. The average spread time of all ATD patients was $2.20\pm1.10$ sec (Table 1), which was significantly slower than normal subjects. Treatment of ATD with punctal occlusion (PO), the spread time in 9 patients was improved to be $0.79\pm0.51$ sec, which was

TABLE 1

Normal Subjects vs. LTD and ATD Subjects With or Without Punctal Occlusion (PO)

| | Spread time (sec) | Tear Stability | Pattern of Spread | Evenness | Thickness (nm) |
|---|---|---|---|---|---|
| Normal (n = 11) | 0.36 ± 0.22 | Stable | Horizontal | Even | 79.1 ± 13.0 |
| LTD (n = 8) | 3.54 ± 1.86 | Unstable | Vertical | Uneven | 53.8 ± 20.0 |
| ATD (n = 17) | 2.20 ± 1.10 | Less stable | Vertical or Mixed | Uneven | 74.1 ± 50.0 (Spot A) 84.7 ± 60.8 (Spot B) 105 ± 85.0 (Spot C) 150 ± 83.6 (Spot D) |
| PO (n = 9) | 0.80 ± 0.50 | Stable | Toward Horizontal | More even | 80.0 ± 17.3 (Spot A) 77.8 ± 19.9 (Spot B) 62.2 ± 17.2 (Spot C) 87.8 ± 35.3 (Spot D) |

[Note]: PO: punctal occlusion, a procedure to treat ATD.

Normal Subjects

Figure 3:
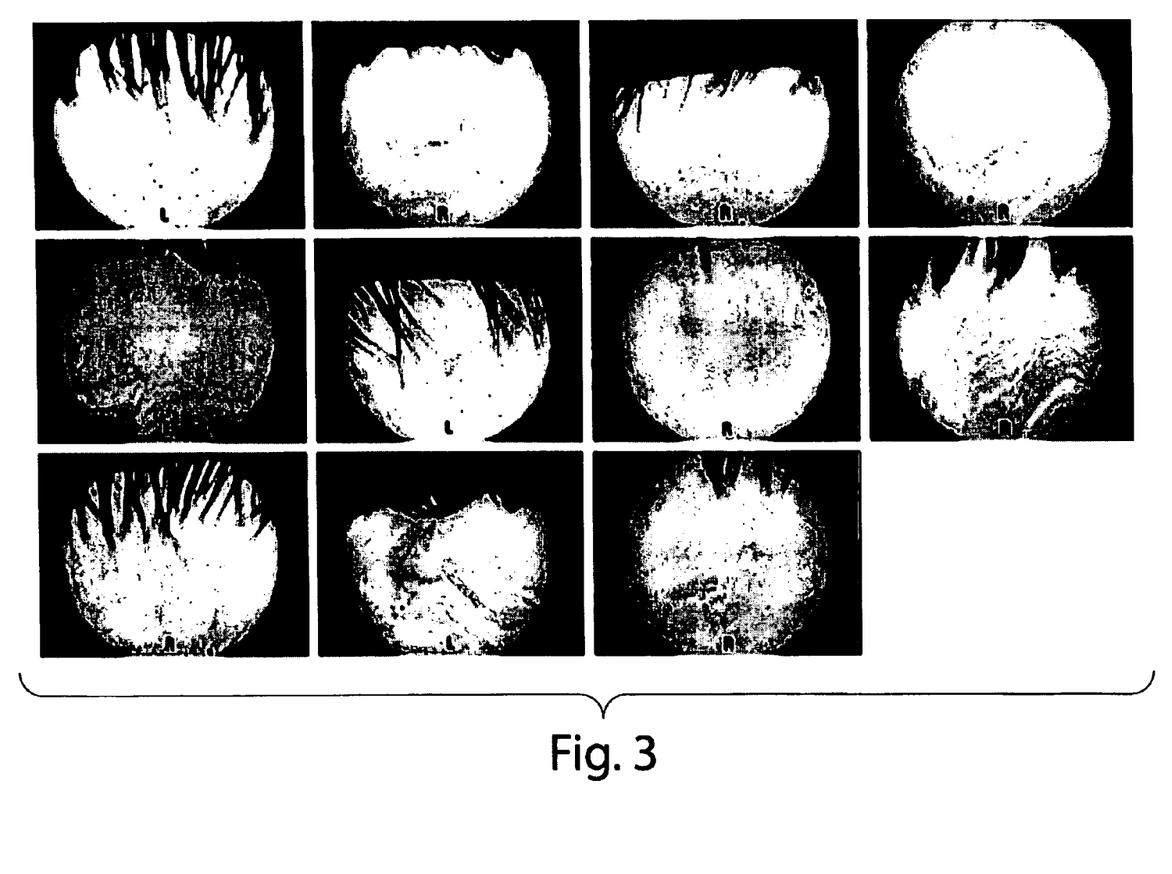
FIG. 3 is a series of tear interference images, showing a normal spread pattern, using the preferred embodiment illustrated in FIG. 2.

As shown in FIG. 3, after blinking, the lipid film spreads rapidly in a horizontal propagating waves from the lower cornea to the upper cornea. Within a short period of $0.360\pm0.22$ sec, the lipid film reached a stable image. During this period of time, the interference of the lipid film yielded a color of gray to white and was uniform and even, meaning that it was well distributed throughout the entire 8 mm in diameter of the central corneal surface. The estimated thickness from LUT was $79.1\pm13.0$ nm. As shown in FIG. 5a, a color intensity histogram distributed at $160.4\pm18.5$.

LTD Patients

Figure 4:
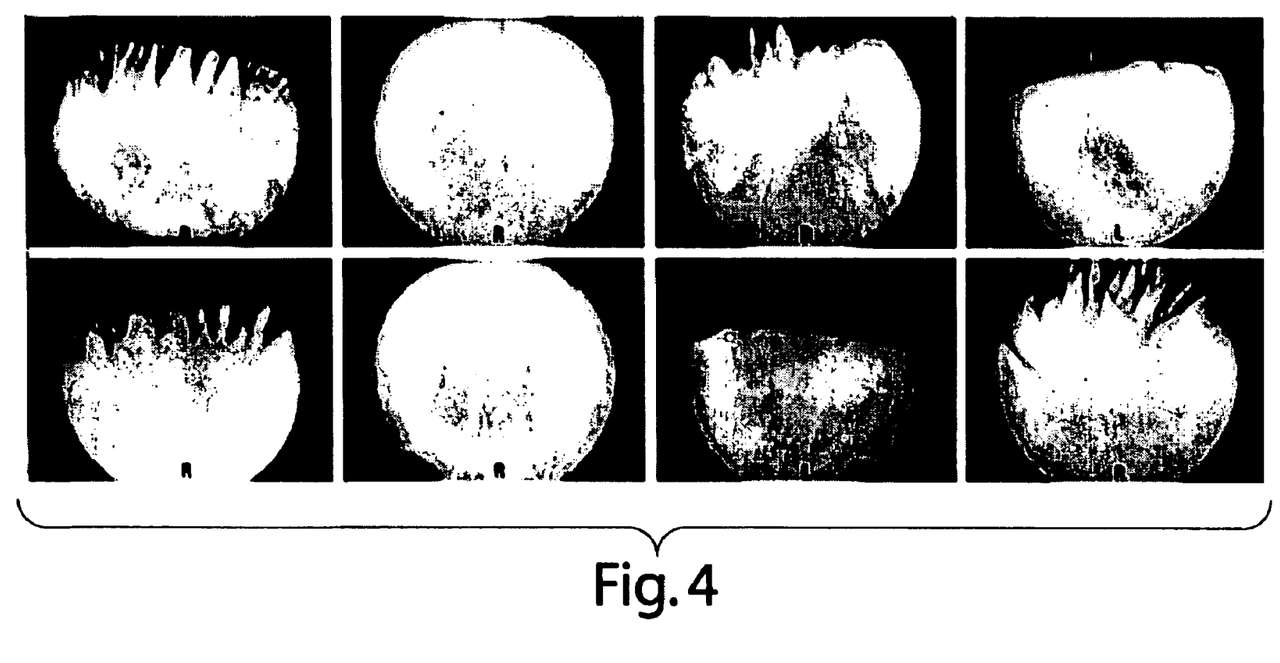
FIG. 4 is a series of tear interference images, showing an abnormal spread pattern, using the preferred embodiment illustrated in FIG. 2.

As shown in FIG. 4, after blinking, faint vertical streaking waves follow immediately from the lower cornea to the upper cornea. Pattern difference is significant (p=0.0000).

In LTD, lipid spread from lid margin is not fully observed. From only certain portions of the lid margin the lipid film starts to spread. Vertical streaking waves are observed. From a very early eye opening time, a dark uniform layer is significantly shortened as compared to the pre-PO values of $2.34\pm1.13$ sec (p=0.008).

Due to the slower spread in ATD patients, the resultant lipid film was found to be thicker on the inferior cornea than the superior cornea. This uneven distribution was clearly demonstrated when four different spots along the vertical meridian (i.e., 12 O'clock to 6 O'clock) were compared in each patient. As shown in Table 1, the thickness at Spots A, B, C and D was $74.1\pm50.0$ nm, $84.7\pm60.8$ nm, $105\pm85.0$ nm, and $150\pm83.6$ nm, respectively, in all patients. These values reflect an uneven distribution of the lipid film thickness along the vertical meridian (p=0.01; the difference between Spot A and Spot D was p<0.01). Nevertheless, the distribution of the lipid film became increasingly more uniform after PO, since the thicknesses at Spots A, B, C, and D became $80.0\pm17.3$ nm, $77.8\pm19.9$ nm, $62.2\pm17.2$ nm, and $87.8\pm35.3$ nm, respectively (p=0.2).

Based on the tear interference images taken at the time when a stable image was reached, three groups were recognized among 17 patients. Group A included cases, where the superior cornea was predominantly covered by a thin lipid film having a color of dark gray, thereby indicating an average thickness of 50.0±11.5 nm. All Group A cases had a vertical streaking pattern in the superior cornea. In addition to a move, rapid spread, the resultant lipid film became thicker in the superior cornea and more uniform after PO. Group B consisted of cases in which the lipid film was thicker than that of Group A on the superior cornea, giving rise to a color of bright gray to white, further indicating an average thickness of 76.7±20.8 nm. Such a thickness was within the range of the normal (79.1±13.0 nm). However, a vertical streaking pattern, not noted in normal subjects, was clearly observed in this region (FIG. 4). Group C included cases in which the lipid film on the superior cornea became more colorful, yielding a average thickness of 133±78.5 nm. A vertical streaking pattern was visible in several Group C cases. After PO, other than the aforementioned changes of thickness and distribution, we also noted that the vertical streaking pattern on the superior cornea was changed to a horizontally propagating pattern, as seen in normal subjects.

Collectively, kinetic analysis and image analysis of tear interference provide additional information with respect to the pattern and speed of lipid spread, the uniformity evenness and thickness of lipid film when the spread is completed, and the stability and duration of a stable image can be maintained after the spread. This new way of analyzing tear interference can help correlate with other non-invasive tests that measure tear film stability, such as xeroscope and tear evaporation. The use of the apparatus and method of the present invention enhances the capability to investigate the mechanism by which an unstable tear film is formed in dry eye. Moreover, kinetic analysis of tear interference is useful in devising and monitoring new therapies that are directed to restoring meiboimian gland functions.

Although only a few exemplary embodiments of the present invention have been described in detail above, those skilled in the art will readily appreciate that numerous modifications to the exemplary embodiments are possible without materially departing from the novel teachings and advantages of this invention. Accordingly, all such modifications are intended to be included within the scope of this invention as defined in the following claims.

What is claimed is:

1. An apparatus for the kinetic analysis of at least one of lipid film spread and tear film interference on a cornea, comprising:
   a light source for illuminating said film of a cornea with light;
   a first light polarizer and a quarter-wave plate lying in a path of said light, between said light source and said cornea;
   a second light polarizer and said quarter-wave plate positioned between said cornea and an image recorder, said image recorder comprising a camera and a processor;
   a frame grabber coupled to said image recorder, the frame grabber positioned to capture a sequence of a series of images of said illuminated cornea, and wherein the processor comprises frame-grabbing software configured to record said series of images during an entire inter-blink interval; and
   an image output for providing said series of images to a display, said series of images illustrating at least one of tear film and a lipid film dispersion pattern indicative of a tear stability condition.

2. The apparatus according to claim 1 wherein said film is located over a central portion of said cornea.

3. The apparatus according to claim 1 wherein said image recorder is coupled to a memory unit to store said series of images.

4. The apparatus according to claim 1 wherein said film dispersion pattern is a propagating pattern of lipid spread.

5. The apparatus according to claim 1 wherein said film dispersion pattern includes color distribution information.

6. The apparatus according to claim 1 in which said quarter-wave plate converts to circularly polarized light the light from said first light polarizer; and converts image from said cornea to linearly polarized light.

7. A method of analyzing the kinetics of at least one of a lipid film spread and a tear film of an eye, said method comprising the steps of:
   modifying light by an optical train to produce a first modified light;
   illuminating said tear film on a cornea of said eye with said first modified light;
   allowing said first modified light to carry an image from the cornea;
   modifying said first modified light carrying an image from the cornea by the optical train to produce a second modified light;
   capturing a sequence of a series of tear interference images of said illuminated cornea with a frame grabber coupled to an image recorder;
   recording said series of images during an entire inter-blink interval with frame-grabbing software;
   outputting said series of images to a display, said series of images illustrating at least one of a lipid film spread and a tear film dispersion pattern indicative of a tear stability condition;
   determining at least one of the direction of lipid spread during the inter-blink interval until a stable pattern is reached or until the next blink, the speed of lipid spread during the inter-blink interval until a stable dispersion pattern is reached or until the next blink, the thickness of the lipid film when the lipid spread is completed, and the stability of the tear film.

8. The method according to claim 7 wherein said illuminating is of a central portion of said cornea.

9. The method according to claim 7 wherein said image recorder is a video recorder.

10. The method according to claim 7 wherein said outputting of said series of images is from said image recorder.

11. The method according to claim 7 wherein said outputting forms said display upon a computer monitor.

12. The method according to claim 7 wherein said outputting is to a television.

13. The method according to claim 7 wherein the occurrence of lipid spread in horizontal propagating streaking waves from the lower cornea to the upper cornea is indicative of tear stability; the occurrence of lipid spread in vertical propagating streaking waves from the lower cornea to the upper cornea is indicative of tear instability;
   wherein if the tear lipid image does not achieve a stable pattern during the inter-blink interval, the tear is designated unstable; and if the tear lipid image achieves a stable pattern during the inter-blink interval the tear is designated stable; and
   wherein if the pattern of lipid spread is vertical from the lower cornea to the upper cornea and the thickness of the lipid film is less than that of a normal subject, the results are indicative of lipid tear deficiency.

14. A method of analyzing a tear film dispersion pattern comprising:

obtaining a kinetic recording of a tear film during an inter-blink interval using tear interference;

displaying an image extracted from the kinetic recording;

determining at least one of the direction of tear lipid spread during the inter-blink interval until a stable pattern is reached or until the next blink, the speed of tear lipid spread during the inter-blink interval until a stable pattern is reached or until the next blink, and the thickness of the tear lipid film when the tear lipid spread is completed.

15. The method according to claim 14, wherein a horizontal propagating lipid spread from the lower cornea to the upper cornea is indicative of tear stability; a vertical propagating lipid spread from the lower cornea to the upper cornea is indicative of tear instability;

wherein if the tear lipid image does not achieve a stable pattern during the inter-blink interval, the tear is designated unstable; and if the tear lipid image achieves a stable pattern during the inter-blink interval the tear is designated stable; and wherein if the pattern of lipid spread is a vertical pattern from the lower cornea to the upper cornea and the thickness of the lipid film is less than that of a normal subject, the results are indicative of lipid tear deficiency.

* * * * *